(12) United States Patent
Blomberg et al.

(10) Patent No.: US 6,794,877 B2
(45) Date of Patent: Sep. 21, 2004

(54) APPARATUS AND METHOD FOR ANALYTICAL DETERMINATIONS

(75) Inventors: Scott Everett Blomberg, Plymouth, MN (US); Kee Van Sin, Line Lakes, MN (US); Brian Anthony Ott, New Brighton, MN (US)

(73) Assignee: International Technidyne Corporation, Roseville, MN (US)

(*) Notice: Subject to any disclaimer, the term of this patent is extended or adjusted under 35 U.S.C. 154(b) by 16 days.

(21) Appl. No.: 10/210,661

(22) Filed: Jul. 31, 2002

(65) Prior Publication Data

US 2004/0021469 A1 Feb. 5, 2004

(51) Int. Cl.[7] .................... G01N 27/416; G01N 33/72
(52) U.S. Cl. ............................. 324/434; 436/66
(58) Field of Search ............................ 324/434, 426, 324/425, 439, 71.1, 692, 722; 204/400, 402, 406, 415; 205/778, 781.5; 422/44, 56, 61, 67, 82.01, 82.02; 436/16, 63, 66, 68, 178

(56) References Cited

U.S. PATENT DOCUMENTS

| | | | |
|---|---|---|---|
| RE30,007 E | | 5/1979 | Steuer et al. |
| 4,469,593 A | * | 9/1984 | Ishihara et al. ............ 210/96.2 |
| 4,484,135 A | * | 11/1984 | Ishihara et al. ............ 324/71.1 |
| 4,686,479 A | | 8/1987 | Young et al. |
| 4,818,361 A | | 4/1989 | Burgess et al. |
| 5,112,455 A | | 5/1992 | Cozzette et al. |
| 5,531,878 A | * | 7/1996 | Vadgama et al. ........... 205/778 |
| 5,633,169 A | * | 5/1997 | Young et al. ................. 436/68 |
| 5,731,212 A | * | 3/1998 | Gavin et al. ................ 436/526 |
| 5,869,971 A | | 2/1999 | Sherman |
| 6,066,243 A | | 5/2000 | Anderson et al. |
| 6,228,652 B1 | * | 5/2001 | Rodriguez et al. ............ 436/63 |
| 6,507,401 B1 | * | 1/2003 | Turner et al. ................ 356/436 |
| 2002/0038101 A1 | * | 3/2002 | Avrahami et al. ............. 604/20 |
| 2003/0000833 A1 | * | 1/2003 | Mansouri et al. ........... 204/402 |

* cited by examiner

*Primary Examiner*—N. Le
*Assistant Examiner*—Hoai-An D. Nguyen
(74) *Attorney, Agent, or Firm*—Fish & Richardson P.C., P.A.

(57) ABSTRACT

An apparatus and method for measuring conductance are provided. The method and apparatus are particularly well adapted for use with a removable or replaceable cartridge in a blood analysis system. The apparatus generally involves providing a system having a first, unfiltered, conductance measurement cell and a second, filtered, conductance measurement cell. The preferred method involves relating values measured in the two cells for a whole blood sample and for a known calibrant together, to obtain a value, for example hematocrit, for the unknown whole blood sample.

20 Claims, 5 Drawing Sheets

APPARATUS AND METHOD FOR ANALYTICAL DETERMINATIONS

TECHNICAL FIELD

The present disclosure relates generally to medical diagnostic techniques and equipment. It particularly concerns techniques and equipment for blood analyses. The technology particularly concerns conductance measurements, for example for making hematocrit determinations.

BACKGROUND

Hematocrit (Hct) is the volume percentage of erythrocytes in whole blood. Although the term was originally applied to the apparatus or procedure used to evaluate this percentage, it is now generally used to designate the result of the determination.

More specifically, hematocrit is defined by the ratio of the volume of packed red blood cells to the volume of whole blood. It has traditionally been determined by centrifugation. According to the centrifugation method, a sample of blood is drawn into a capillary tube which is then spun at a high rate in a centrifuge until the solid portion of the blood cells become packed together in one end of the tube. The ratio of volumes is measured by simply measuring the length of: (1) the packed blood cells; and (2) the overall length of the blood sample in the tube, and dividing length (1) by length (2). In this process, length (or volume) is cancelled out and the result is typically reported as a percentage, commonly referred to as the percent packed cell volume or % PCV. This measurement has proven useful for diagnosing and evaluating a number of conditions and diseases, for example anemias.

Hematocrit measurements have also been approximated, based upon electrical conductance measurements. The electrical conductance approach generally has involved establishing a sample flow path or cell configuration that includes an electrode arrangement typically comprising two spaced electrodes of a material inert to the blood and the conditions of the conductance measurement, typically gold. The electrodes are disposed in a precisely defined, spaced, relation, so as to enable measurement of conductance of a fluid introduced between, and in contact with them. In one typical approach, the size and position of the electrodes and the size and shape of the flow path (cell) are precisely controlled. Under such circumstances, the conductance can be measured and the hematocrit can then be calculated based upon a predetermined (empirically derived) calibration curve (for example a least squares line) relating conductance to hematocrit for the same cell.

The above described approach to evaluating hematocrit has been based upon an observation that, in general, blood cells are not very conductive. Thus, the more volume that is taken up by blood cells within the space between the electrodes, the higher is the resistance (or lower is the conductance) of the system.

In the medical industry, it has become desirable to conduct analytical evaluations using easily handled sample cartridges. Such cartridges are manufactured in lots comprising a large number of cartridges. As a result, approaches to hematocrit evaluations that do not rely upon a precise controlling, and modeling, of the size and shape of the cell have been developed. Typically for such circumstances, a conductance ratio is developed based on: (1) measuring the conductance of a standard (or calibration) material of known or predetermined conductance introduced into the volume between the two electrodes, and, (2) also measuring the conductance of a blood sample placed in the same cell or location. From this, a conductance ratio is developed and calculated; for example by dividing the sample conductance (2) by the standard solution conductance (1). The division cancels out certain factors from variations due to the specific size and shape of the cell.

The conductance ratio is then used to determine hematocrit (Hct), from a predetermined calibration curve (for example a line) for the standard calibration solution and the cell. This approach reduces the need to precisely control the size and shape of the electrodes and the flow path. Alternately stated, using a ratio or relationship between an unknown blood solution, and a known calibrant or calibration solution, and then comparing the ratio to a previously established calibration curve for the same calibrant, allows measurement of hematocrit while canceling out variability from cell size, electrode shape, etc., between manufacturing batches, etc.

Substances in blood plasma, or variations in properties of blood plasma, can influence conductivity. That is, there are blood variables that affect conductivity other than from erythrocytes. For example, the concentration of electrolytes in the blood plasma can vary greatly from sample to sample (patient to patient). This can affect the calculated hematocrit result when the above described conductance ratio approach is used, since this variable is not managed or accounted for in the approach. Alternately stated, electrolyte variability in the blood sample, for example from patient to patient, can affect the conductance measurements. However, in general it is not possible to adjust for that variability, in preparation of the calibration solution. Thus, the resulting ratio discussed in the previous paragraph will not cancel out that variable, and it will be carried over into the final hematocrit calculation.

Attempts have been made to deal with this variable. For example, according to U.S. Pat. No. 4,686,479, the concentration of electrolytes in the blood is measured; and, for the hematocrit measurement, the measured electrolyte concentration is used in performing a mathematical correction to the result from conductance measurements to determine the blood conductivity. Problems with this approach include: the inherent possible variability of the needed additional blood electrolyte sensors; and, the fact that certain electrolytes may not be measured and therefore would not be included in the correction factor.

Improvement in hematocrit measurements is desired. What is particularly desired is a convenient, reproducible, approach to provide a reasonably consistent evaluation of hematocrit, from conductance type measurements. Also, an apparatus to apply the approach, is needed.

SUMMARY OF THE INVENTION

According to the present disclosure, techniques and equipment are provided for making conductance measurements to evaluate an unknown, for example, whole blood, sample. In general, the equipment can be applied to provide: a first, unfiltered, conductance measurement cell; and, a second, filtered, conductance measurement cell. In a typical arrangement the two cells are positioned for contact by a single sample, at the same time. A typical arrangement, as described, includes using a red blood filtered cell as the second, filtered, cell and positioning the arrangement as a hematocrit measurement arrangement in fluid flow communication with a liquid sample inlet in the same cartridge.

In a typical sample analysis cartridge (including the hematocrit measurement arrangement as characterized) the second, filtered, conductance measurement cell comprises a pair of spaced electrodes positioned in, or underneath, a filter, with the filter being selected, for example, to filter red blood cells, from reaching the region between the two spaced electrodes. In such an embodiment, the second conductance measurement cell will typically comprise a pair of gold electrodes each having an electrode surface area of no more than 0.04 in$^2$ (25.8 sq. mm.). In certain embodiments described, the electrode surface area would typically be about 0.01 in$^2$ (6.4 sq. mm.) to 0.02 in$^2$ (12.9 sq. mm.) inclusive. Also, in typical systems the electrodes would be spaced apart from one another by a distance of no greater than 0.005 inches (0.127 mm.); and, for certain embodiments described they would be spaced apart a distance within the range of 0.0001 inch (0.025 mm.) to 0.002 inch (0.051 mm.) inclusive. In some embodiments the electrodes of the red blood cell filtered cell are spaced apart less then 50 microns.

A variety of configurations for the first conductance measurement cell are possible. In one embodiment, the first, unfiltered, conductance measurement cell comprises a pair of electrodes positioned spaced from one another, each of which is preferably a gold electrode having an electrode surface area of no greater than 0.5 in$^2$ (322 sq. mm.). In certain embodiments described the area would be within the range of 0.2 in$^2$ (129 sq. mm.) to 0.3 in$^2$ (196 sq. mm.) inclusive. For a typical arrangement the two electrodes of the first conductance cell are spaced apart from one another by distance of no greater than 1.00 inch (25.4 mm.), typically 0.25 inch (6.35 mm.) to 0.5 inch (12.7 mm.) inclusive. In an alternate embodiment, a single electrode may be positioned in the first, unfiltered, conductance measurement cell.

The measurement arrangement characterized can be conveniently positioned within a removable and replaceable sample analysis cartridge, for example a cartridge (typically having a size no greater than about 100 sq. cm., usually no greater than 80 sq. cm., and preferably 50 sq. cm., or less) that can be removably and replaceably positioned within an analytical base station, for use.

The filter for the filtered cell, may comprise a hydrogel. In an alternative, it can comprise, for example, a microporous membrane. Also, the filter can be the result of providing electrodes within the cell so close, that material such as red blood cells to be filtered cannot get between them and thus are filtered out. In this latter embodiment, the electrodes would typically be covered by a dielectric material, with a cut or slit, that operates as the filter material.

In general, according to the present disclosure, a method is provided for evaluating an unknown whole blood sample. In general, the method includes a step of measuring conductance of a known whole blood sample in a hematocrit measurement system as characterized above. A conductance value from the first, unfiltered, conductance measurement cell and a conductance value from the second, filtered, conductance measurement cell, can be correlated to determine a value, for example hematocrit, for the unknown whole blood sample. In a preferred process, the step of correlation includes correlating with conductance values determined for a known calibrant in the first, unfiltered, conductance measurement cell and the second, filtered, conductance measurement cell.

A particular technique of correlating described herein involves the following steps:

1. Measuring a conductance value ($C_B$) in the first unfiltered cell, for an unknown whole blood sample;

2. Measuring a conductance value ($C_P$) for the unknown whole blood sample, in the second, red blood cell filtered, conductance measurement cell;

3. Measuring a conductance value ($C_C$) for a known conductance calibrant, in the first, unfiltered, conductance measurement cell; and 4. Measuring a conductance value ($C_{CF}$) for the known conductance calibrant in the second, red blood filtered, conductance measurement cell.

5. Determining a value $R_B$ according to the formula: $R_B=C_B/C_C$.

6. Determining a value $R_P$ according to the formula: $R_P=C_P/C_{CF}$.

7. Determining a value $R_G$ according to the formula: $R_G=R_B/R_P$.

8. Determining a hematocrit value based on the calculated value of $R_G$, by comparison to an emperically derived curve.

For example, once $R_G$ has been determined, the hematocrit value can be based upon a relationship such as the following:

$$\text{Hematocrit}=R_G(C1)+C2,$$

wherein C1 and C2 are constants derived for the hematocrit measurement system using a known calibrant.

Alternate functions utilizing $C_P$, $C_B$, $C_C$, $C_{CF}$ or even $R_G$ are possible, to calculate hematocrit. The particular approach described, is a convenient approach that is relatively straight forward to implement. The order of steps, as explained below, is not, typically, critical.

DETAILED DESCRIPTION

Figure 1:
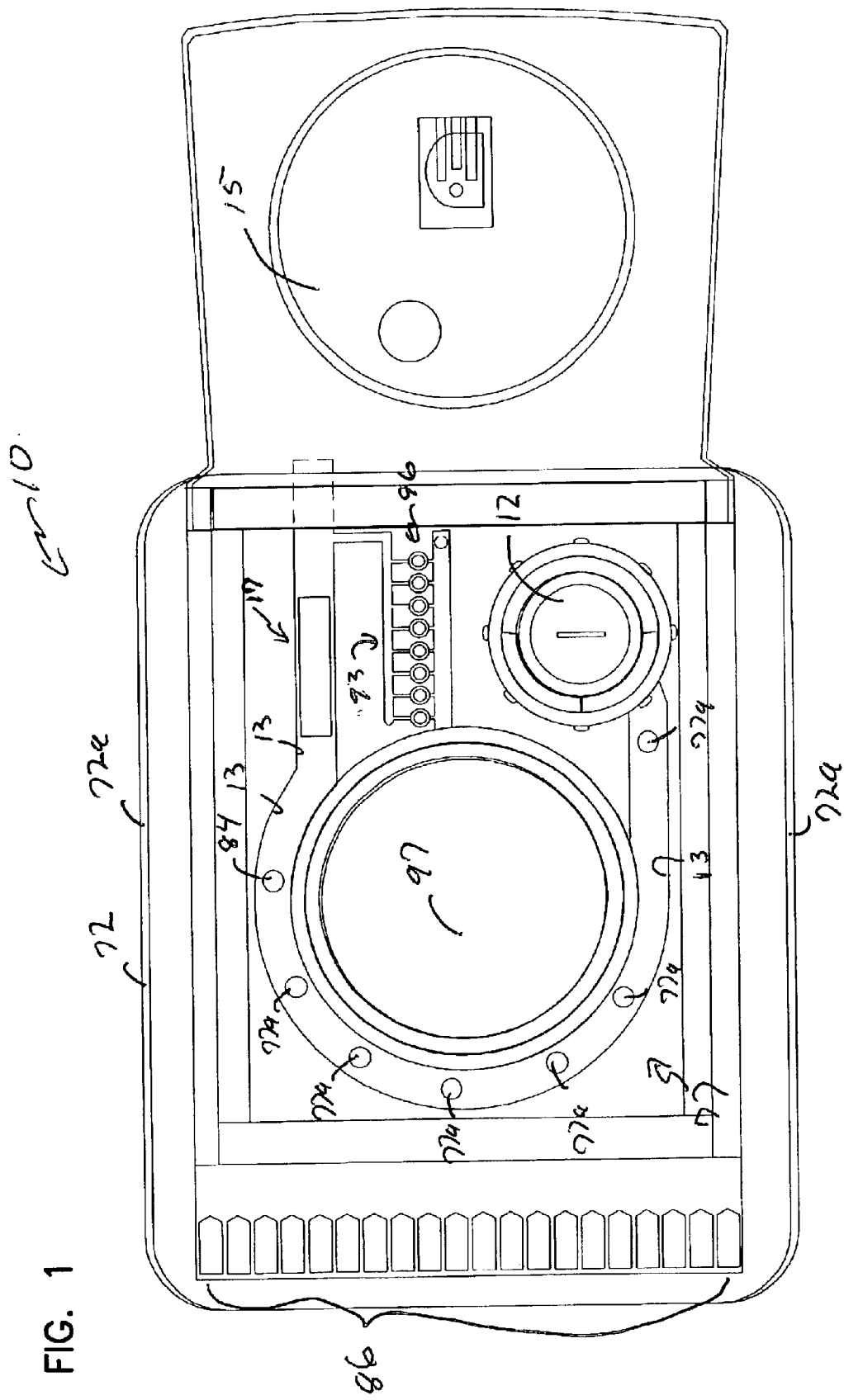
FIG. 1 is a schematic diagram of an analysis cartridge useable for evaluating conductance characteristics, of a fluid sample, in accord with the present disclosure.

I. General Structural Features of A System for Measuring Hematocrit via a Conductance Approach.

In general, the techniques and equipment described herein are adaptable for use with a analytical base station/cartridge system in which a relatively small, removable and replaceable, cartridge is used and into which is placed a liquid sample (typically blood) to be analyzed, during use. The cartridge is then connected to, or is inserted into, an analytical base station (or module), during use, for conduct of an analytical analysis. Two commercially available types of analytical base stations or systems, adaptable for implementation of the techniques described herein, are the IRMA Blood Analysis System (IRMA) and the Blood Analysis Portal System (PORTAL), both of which are available for Diametrics Medical, Inc. of Roseville, Minn. 55113, the assignee of the present application.

General features of analytical systems such as IRMA and PORTAL are characterized, for example, in U.S. Pat. No. 6,066,243 ('243), assigned to Diametrics Medical, Inc. The complete disclosure of the '243 patent is incorporated herein by reference. Improved features of liquid sample cartridges useable with such arrangements are described in: (a) the co-pending U.S. patent application filed May 30, 2002 entitled "Cartridge Arrangement, Fluid Analyzer Arrangement, and Methods;" the application having been deposited in the U.S. Post Office addressed to the U.S. Patent Office with Express Mail label number EV 077889628 on May 30, 2002 with identification of the following inventors: John Herbert Thornberg; Kee Van Sin; Martin Gaines Hieb; Ronald William Sand; and Scott Everett Blomberg, and assigned application Ser. No. 10/160,329; and, (b) co-pending U.S. patent application (U.S. appl. Ser. No. 10/185,201) filed Jun. 28, 2002, entitled "Analytical Test Cartridge; and Methods," and having been deposited in the U.S. Post Office addressed to the U.S. Patent Office with Express Mail label number EV 077889605 on Jun. 28, 2002, with identification of the following as inventor: Kee Van Sin. The co-pending application identified above in this paragraph at (a) will be referenced herein as the "Thornberg, et al. application." The copending application identified above in this paragraph at (b) will be referenced herein as the "Kee Van Sin application." The "Thornberg, et al. application," and the "Kee Van Sin application" are both owned by Diametrics Medical, Inc., the assignee of the present disclosure, and each is incorporated herein by reference, in its entirety.

The sample cartridges characterized in the Thornberg, et al. application and the Kee Van Sin application preferably have a perimeter area no larger than 100 sq. cm., typically no larger than 80 sq. cm., and are usually of a size of about 50 sq. cm., or smaller. Typically, such cartridges are no more than 3 cm. high (discounting any attached syringe). Generally, each includes: a sample fluid injection port and container; various sensors for conduct of analytical analyses of a liquid sample injected into the injection port; various electrical leads for communication with electronic equipment within an analytical module or base station for control of analytical testing and communicating data and/or results; and, various mechanical structure to facilitate mounting or removal of the cartridge with respect to the analytical equipment.

In general, such analytical cartridges have relatively short useful lifetimes, with respect to the expected lifetime of the analytical componentry with which they are used. As a result, such cartridges are sometimes referred to as "disposable cartridges" or "disposable test cartridges." Indeed, in many instances, the cartridges are single-use cartridges.

Referring to FIG. 1, an analytical cartridge 10 is depicted (schematically). Cartridge 10 includes a sample inlet construction or port 12 into which a liquid sample to be evaluated can be inserted. It is anticipated that for many uses, the sample will be initially contained in a syringe, in which case the inlet port 12 can be provided with either a Luer-lock or other lock or engagement structure, to facilitate engagement with a syringe, for fluid transfer from the syringe into the cartridge 10 without spillage.

The cartridge 10 includes and defines a flow channel or chamber 13. In this instance the flow chamber 13 is in communication with, and extends between, the inlet 12 and an opposite fluid terminus or fluid flow reservoir 15.

Within the fluid flow channel or chamber 13 is positioned a conductance measurement arrangement or system 17, in this instance a hematocrit measurement system. The hematocrit measurement system 17 is described below, in connection with the description for FIGS. 2–5, 7 and 8. Before additional features relating to the cartridge 10, FIG. 1, are discussed, the hematocrit measurement system 17 will be described in detail.

Referring still to FIG. 1, it is again noted that the hematocrit measurement system 17 is shown positioned within the fluid flow channel 13. In general, alternate configurations are possible. What is preferred, is that the hematocrit measurement system 17 be in fluid flow communication with the inlet port 12, to appropriately receive a sample therein, for hematocrit measurement. This will be apparent from the following descriptions.

Figure 2:
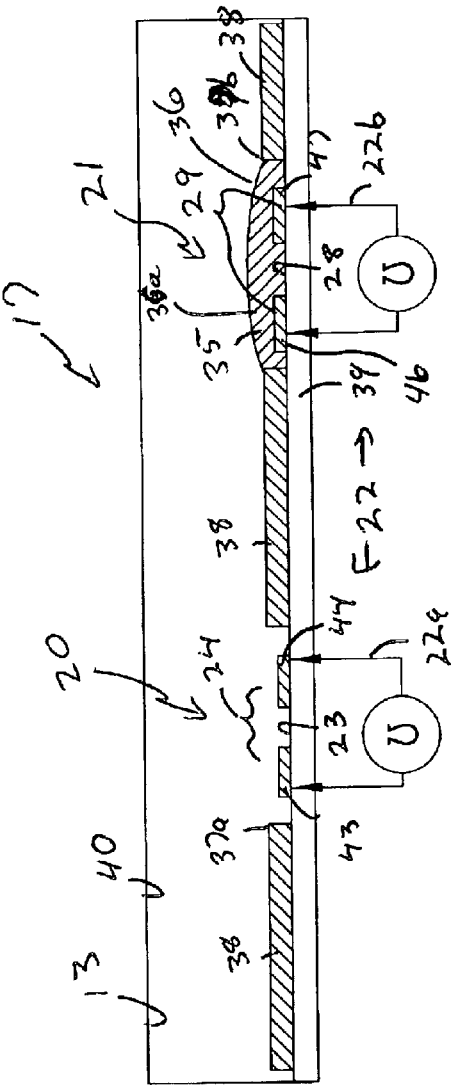
FIG. 2 is a schematic diagram of an analysis arrangement for evaluating conductance characteristics in accord with the present disclosure.

Attention is now directed to FIG. 2, in which is depicted (schematically) the conductance measurement arrangement or system 17. Referring to FIG. 2, the arrangement 17 is depicted in fluid flow channel 13, and comprises first and second conductance (resistance) measurement regions or cells 20 and 21, respectively. In FIG. 2, circuitry 22 is also shown, comprising a first portion 22a and a second portion 22b. The conductance measurement system may be used to measure various characteristics but it is especially well adapted for evaluation of hematocrit.

In general, the first conductance (or conductivity) measurement cell 20 is in fluid flow communication with the sample inlet port 12, includes an electrode arrangement 24 therein and defines a sample receiver volume 23. Similarly, the second conductance (or conductivity) measurement cell 21 includes an electrode arrangement 29 therein and defines a sample receiver volume 28. An important difference between the first conductance measurement cell 20 and the second conductance measurement cell 21 is that the second conductance measurement cell 21 is a filtered cell, i.e., it is constructed and configured such that a fluid sample cannot reach the electrode arrangement 29 therein, without being filtered, for example by passing through filter 35. Preferred materials and/or arrangements for filter 35 will be described below. In general filter 35 is configured to inhibit or prevent certain types of materials or blood components (especially red blood cells when used for hematocrit evaluations) from entering sample receiver volume 28 and engaging electrode arrangement 29. In FIG. 2, filter 35 comprises filter material 36, positioned to cover electrode arrangement 29.

Herein the first conductance measurement cell 20 will sometimes be referred to as a "unfiltered" cell, since the liquid can enter the cell 20, from inlet port 12, without being filtered for removal of red blood cells. On the other hand, the second conductance measurement cell 21 will sometimes be referred to herein as a "filtered cell" or "red blood cell filtered cell," (or by variants thereof) to indicate that a blood sample cannot enter the cell 21, for conductance measurements, without being filtered for substantial removal of selected material (for example red blood cells) there from. Advantages from use of both a filtered cell 21 and an unfiltered cell 20 in the same hematocrit measurement system 17, will be apparent from further descriptions below.

Referring to FIGS. 1 and 2, it is again noted that the hematocrit measurement arrangement or system 17 is depicted schematically. No specific distance relationship between the first conductance measurement cell 20 and the second conductance measurement cell 21, is meant to be implied by the schematic drawings. In FIG. 1, the system 17 is depicted in a particular location within chamber 13. However, the two cells 20, 21 could be positioned at different locations within channel 13, and need not be adjacent to one another. Further, other components, such as sensors discussed below, could be positioned between the two cells 20, 21. In addition, there is no particular order to be implied, with respect to which of cells 20, 21 is encountered first in fluid flow through channel 13 from inlet port 12. Thus, cell 20 could be positioned in the flow path before channel 21, or after cell 21.

In general, the hematocrit measurement arrangement or system 17, in a typical cartridge 10 according to the present disclosure, is configured so that when a blood sample is introduced into port 12, the blood sample will contact electrode structure 24, 29 within both cells 20 and 21. Preferably the cartridge is configured such that injection of a total unknown (for example blood) sample having a volume of about 3 milliliters (ml) or less, typically 200 microliters ($\mu$l) or less, will be adequate to accomplish this. Typically and preferably the hematocrit measurement arrangement or system 17 will be sized such that no more than 200 $\mu$l., typically no more than 150 $\mu$l. of sample, for example blood, (for example 30 to 100 $\mu$l.), within channel 13 is needed to accommodate the operation of the cells 20, 21 as described below. This latter amount will sometimes be referred to as the operational sample volume. Referring to FIG. 2, this means simply that to cover the cells 20, 21, typically no more than 200 $\mu$l., preferably no more than 150 $\mu$l., (and more preferably no more than 30–100 $\mu$l) of the sample is needed to at least extend between points 37a and 37b.

Still referring to FIG. 2, reference numeral 38 generally depicts regions of dielectric material usable to help define the cells 20, 21; and numeral 39 depicts base structural material (for example a ceramic substrate) of cartridge 10.

Now consider the region 40 of flow conduit 13, i.e., the portion which includes system 17, FIG. 2, when filled with a blood sample, for hematocrit measurement. A portion of the blood sample will fill, by flow into region 23, the first conductance measurement cell 20. Some materials within the blood sample will also fill the second conductance measurement cell 21, by flow into region 28. However, if appropriately chosen, the filter 35 will prevent certain components (especially red blood cells) within the blood sample from filling the cell 21 and engaging electrode arrangement 29. In particular, what is preferred, is to select the filter 35 such that red blood cells are inhibited from entering cell 21.

In general, red blood cells have a size on the order of about 6–8 microns, and white blood cells on the order of about 6–10 microns. The filter 35 should comprise of material 36 which inhibits passage of red blood cells (and typically also white blood cells) therethrough, to reach the electrode. For example, a hydrogel or a porous filter media such as porous polycarbonate, could be used. Some alternate configurations for the filter 35 are also described below. In general, a filter 35 or filter material 36 appropriate for inhibiting red blood cells from entering cell 21, but typically otherwise permitting blood plasma, inorganic electrolytes, proteins and similar materials from entering cell 21, will be referred to herein as a "red blood cell filter material 36a."

Still referring to FIG. 2, it is noted that red blood cell filter material 36a is positioned in a relation "covering" electrode arrangement 29 within cell 21. That is, the electrode arrangement within cell 21 cannot be contacted by fluid that is not passed through red blood cell filter 36a. In some instances, such an arrangement between the red blood cell filter material 36a and the electrode arrangement 29, will be described herein by, for example, a characterization such as "the electrode arrangement 29 is positioned underneath the red blood cell filter material 36a;" or "the electrode arrangement 29 is positioned covered by, protected by, or shielded by, the red blood cell filter material 36a," or by variants thereof.

A comparison of conductance (for a whole blood sample) between the first conductance measurement cell 20 and the second conductance measurement cell 21, can be used to evaluate, or be correlated to, hematocrit. For example, a measurement of the difference in conductance between cell 20 and cell 21, for a whole blood sample, could be directly compared to empirically derived measurements for the same cells, using standards. This comparison could then be used to calculate or determine the hematocrit (% PCV) value.

In general, it is anticipated that such an approach will not typically be preferred, since it does not take into account variability introduced into different lots or manufactures of the cartridges 10. Thus, it is expected that for a typical practice, conductance measurements will be made with the arrangement 17 for both: (1) a calibrant or calibration material; and, (2) an unknown blood sample, for any given hematocrit determination.

The term "calibrant" or "calibration material" as used in this context is meant to refer to a material (typically a solution or gel) which has a known conductance. Such a material, as indicated below, can be used to help determine hematocrit for an unknown whole blood sample. Before a description is presented of this, however, further detailed discussion of the hematocrit measurement system 17 depicted in FIG. 2 is presented.

Still referring to FIG. 2, the electrode arrangement 24 of the first conductance measurement cell 20 comprises first and second electrodes 43 and 44. For a typical system, the electrodes 43 and 44 will be selected from a material neutral to the conditions of operation of the cell 20. An example would be to use a pair of gold electrodes, for electrodes 43 and 44. For a typical system, each of electrodes 43 and 44 would have an electrode surface area or size of no larger than about 0.5 in$^2$ (322 sq. mm.). For an embodiment such as shown in FIG. 2, the size would typically be within the range of 0.2 in$^2$ (129 sq. mm.) to 0.3 in$^2$ (196 sq. mm.), inclusive. Typically, the electrodes 43, 44 would be spaced apart from one another by a distance no greater than 1 inch (25.4 mm.). For an embodiment as shown in FIG. 2, typically this distance would be within the range of 0.25 inch (6.35 mm.) to 0.5 inch (12.7 mm.) inclusive. (The term "inclusive" in this and similar contexts means that the end points are included in the stated typical or preferred range.) In this context, the electrode surface size of an electrode refers to an area of a surface which is available to operate in direct contact with the blood sample.

Similarly, the electrode arrangement 29 of the second conductance measurement cell 21, comprises two electrodes 46 and 47. Again, electrode material (for example gold) neutral to the environment of use will be preferred. For a typical arrangement, the electrodes 46, 47 would have an electrode surface area or size of no larger than about 0.04 in$^2$ (25.8 sq. mm.). For an embodiment such as that shown in FIG. 2 these electrodes 46, 47 would each have a surface area typically within the range of 0.01 in$^2$ (6.4 sq. mm.) to 0.02 in$^2$ (12.9 sq. mm.), inclusive. Typically, the electrodes 46, 47 would be spaced apart from one another by a distance of no greater than 0.005 inches (0.127 mm). For an embodiment such as shown in FIG. 2, these electrodes 46, 47 would be spaced apart a distance within the range of 0.0001 inch (0.025 mm.) to 0.002 inch (0.051 mm.) inclusive.

In general, conductance is measured in units called "mhos." The unit (mhos) is the same as ohms$^{-1}$, i.e., it is the reciprocal of resistance. An appropriate electrical control system, not shown in FIG. 2, can be used to measure the conductance of a sample positioned between electrodes 43, 44; and/or for a sample positioned between electrodes 46, 47.

Figure 3:
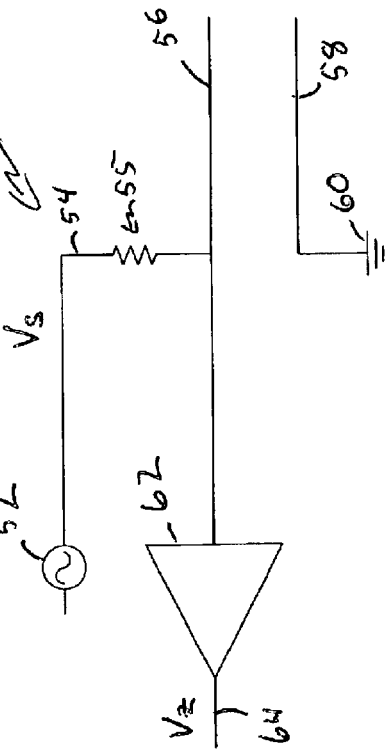
FIG. 3 is a schematic diagram of a conductance measuring circuit usable in the analysis arrangement according to FIG. 2.

In FIG. 3, a schematic diagram of an electric circuit 50, usable to provide conductance or conductivity measurements, for determinations in accordance with the description provided below, is depicted. In a typical arrangement, the electrical circuit 50 would be positioned in an analytical base station used with the cartridge 10, the only portion of the circuit 50 being found in the cartridge 10 being portions of electric leads providing electrical communication to the cells 20, 21.

Referring to FIG. 3, an alternating current source is indicated at 52 and may be a conventional signal generator contained in a base analytical device, as described below. The alternating current, denoted $V_S$, is shown in line 54 with a series resistor 55 having a resistance $R_1$. Leads 56 and 58 provide electrical communication to the cells 20, 21; i.e., to electrode arrangements 24 and 29, FIG. 2. That is, the leads 56, 58 provide for electrical communication between cells 20, 21 and the analytical equipment or base station. A ground connection is shown in 60. The circuit 50 depicted includes an RMS to DC converter 62, the output of which is a DC voltage shown as $V_Z$ on line 64. Of course the circuit 50, provides for circuits 22, FIG. 2.

II. Conductance Measurements; Hematocrit Determinations.

An example of a measurement of conductance using the circuit 50 of FIG. 3 is as follows. Alternating current ($V_S$), possibly 70 kilohertz as an example, is sequentially impressed across electrode arrangement 24 and also electrode arrangement 29 (FIG. 1) utilizing conductors 56 and 58 in series with the resistor 54. The resulting voltage between the resistor and the electrode arrangements 24, 29, would be measured for the pair of electrodes (43, 44 or 46, 47) for each cell 20, 21 respectively. Each would be converted to a DC voltage signal ($V_Z$) through RMS DC converter 62.

The conductance could then be calculated using the following equation:

$$\text{Conductance} = [(V_S/V_Z) - 1]/R_1$$

Wherein, $R_1$ is the resistance of resistor 55, FIG. 3, in ohms.

It is noted that the particular electrode arrangement for the embodiment of FIG. 2, is such that, for a typical operation, the electrodes 43, 44 of cell 20 are operated, to measure conductance, with a circuit 22a that is isolated from the circuit 22b that is used to evaluate the conductance between electrodes 46, 47. Such an arrangement will thus utilize four electrodes (43, 44, 46, 47) and four leads or traces (i.e., channels as discussed below) on the cartridge 10.

In the description below at III, in connection with FIGS. 4 and 5, some alternate configurations usable are presented. Prior to description of them, however, a manner in which conductance measurements (taken as described above in connection with FIGS. 2 and 3), can be used for hematocrit measurements will be presented.

As indicated above, the hematocrit measurement arrangement 17 in FIG. 2, includes two conductance measurement cells 20, 21 therein. The difference between the two cells 20, 21 is that filter 35 is a red blood cell filter and thus prevents the solid or red cell portion of blood from entering the cell 21, whereas there is no such filtering associated with cell 20.

The arrangement 17, then, allows for measurement (for example simultaneously) of: (1) conductance ($C_B$) of an unknown whole blood sample within defined cell 20, to determine whole blood conductance; and, (2) conductance ($C_P$), within a defined cell 21, of the plasma and soluble (and any unfiltered) electrolyte fraction of the unknown whole blood sample (i.e., filtered blood). A direct comparison of the two values (i.e., $C_B$ and $C_P$), allows for comparison of conductance between two defined cells, and the effect of the red blood cell (and white blood cell or other large component) presence on the conductance measurement. (Of course, the filter 35 occupies space. Thus, cells 20 and 21 also differ due to the fact that the membrane occupies volume. Also, the cells and electrodes are not necessarily the same size. As will be apparent from the following descriptions, the preferred process characterized herein, accounts for these types of differences.)

To facilitate hematocrit determination, as indicated above, it is anticipated that in a typical application, a conductance calibrant will also be used. That is, a calibrant will be placed within region 40, to fill sample volumes 23 and 28. Conductance measurements of the calibrant by the first conductance measurement arrangement 24, and the second conductance measurement arrangement 29, can then be used to evaluate hematocrit for the whole blood sample.

In general, herein the conductance (C) measured by a electrode arrangement 24 (of the unfiltered cell 20) of whole blood will be referred to as $C_B$; and the conductance measurement of the plasma (whole blood minus red blood cells and any other filtered material) measured by the electrode arrangement 29 of the filtered cell 21 will be characterized as $C_P$. Similarly, herein the conductance of a calibrant measured in the first conductance measurement cell (the unfiltered cell) 20 by electrode arrangement 24 will be referred to herein as $C_C$; and, the conductance measured in the second (filtered) conductance measurement cell 21 by electrode arrangement 29 will be referred to as $C_{CF}$ (conductance of filtered calibrant).

The manner in which the values of $C_B$, $C_P$, $C_C$, and $C_{CF}$ are used to provide for hematocrit calculation, is a matter of choice that can be varied from system to system. Herein, one particular function, i.e., $f(C_B, C_P, C_C, C_{CF})$, usable to arrive at a hematocrit value for the whole blood sample using the four conductance measurements identified, is provided. The approach described, is meant to be an example of such a function, and it is not intended to be exclusive of alternate calculations or approaches.

In particular, in one preferred approach two initial whole blood/calibrant conductance ratios can be determined. The first is a ratio of whole blood conductance ($C_B$) to calibrant conductance ($C_C$), each measured within unfiltered (or exposed electrode) cell 24. This ratio would typically be the ratio $C_B/C_C$, and is characterized herein as $R_B$. The second ratio is the ratio of conductance of whole blood from the unknown (in the filtered, protected or shielded cell $C_P$) to the conductance of calibrant in the filtered, protected or shielded cell 21 ($C_{CF}$). This is the ratio $C_P/C_{CF}$, and will be referred to herein as $R_P$.

The two ratios $R_B$ and $R_P$, can, for example, be related to produce a grand ratio $R_G$, for example via the following relationship: $R_G = R_B/R_P$.

The grand ratio $R_G$, can be utilized to determine the actual hematocrit according to a defined function; i.e., hematocrit= $f(R_G)$. The function, $f(R_G)$, can be selected from a variety of functions either theoretically or emperically derived. It is anticipated that in a typical application, a curve (or line) relating $R_G$ to % PCV, based upon emperically derived evaluations for the system and calibrant, would be used. The measured value $R_G$, would then be compared to this curve (or line) to determine a % PCV. When it is said that the value $R_G$ is compared to a curve (or line) it is not meant that a physical comparison is necessarily made. A computerized comparison to a mathematically defined function would typically be used. Herein the term "curve" when used to refer to a function or result of a function, is intended to include within its scope "linear" functions or results.

For example, the following equation can be used to relate $R_G$ and Hematocrit.

$$\text{Hematocrit} = R_G(C1) + C2. \qquad \text{Equation I}$$

Wherein, C1 and C2 are constants predetermined through analytical testing. An approach to calculating them is provided below.

More specifically, for Equation I defined above, the constants C1 and C2 represent slope and intercept of a relationship that can be determined (defined) experimentally (empirically) by testing samples of blood or other compositions of known hematocrit (known test samples) over the reportable range of the hematocrit measurement system 17, and comparing those results to data calculated using a standard technique (for example a centrifuge method).

In a typical approach to determine the constants C1 and C2, a number of test samples, typically 3–5, of blood or a similar material would be prepared at defined different levels of hematocrit (generally ranging between 10% and 80% PCV.) A hematocrit measurement cartridge 10 from a production lot of cartridges, for example having a flow path and cell definition for arrangement 17 in accordance with FIGS. 1 and 2, would be calibrated by measuring the conductance of both electrode arrangements (24, 29) by positioning one of the test blood samples or standards (and also at some point a calibrant) over the appropriate electrodes. Sequentially, each individual blood sample would be introduced over the same electrodes and sample conductivity would be measured by both electrode arrangements (24, 29). A grand ratio (RG), based on comparison to a defined standard, would be calculated for each sample. The calibration and sample measurement steps could be repeated for each sample. (If the hematocrit electrodes are contained in a single use disposable cartridge, a new cartridge from the same manufacturing lot could be used for each test sample or calibrant tested). Also, the hematocrit of each test blood sample (% PCV) would be measured using the centrifuge technique.

After the data is collected, the sample hematocrit values from the centrifuge technique (% PCV) would be plotted against the grand ratio (RG) values. A curve or relationship could be produced from the data using a least squares approximate fit, and the constant C1 (slope) and the constant C2 (intercept) could be determined, for cartridges from the same lot and a selected (defined) calibrant. Of course, the grand ratio $R_G$ would have no units. The slope (C1) could be chosen to have units of % PCV; and, intercept (C2) could be chosen have units of % PCV.

In a "best" approach, the identical calibrant would be used for the experiment to define C1 and C2, as would be later used to evaluate an unknown whole blood sample. In the event that this is not possible, the constants (C1 and C2) may need to be redetermined with subsequent productions of calibrant and/or measurement cartridges. However, in some instances it may possible to merely confirm the constant values (i.e., the values of C1 and C2) when new production lots of either calibrant or cartridges are made.

For an unknown blood sample, then, a cartridge from the same lot and a calibrant from the same production of calibrant could be used, along with the defined values C1 and C2 (typically provided in programming of the analytical base station), to determine hematocrit for example in accord with Equation I above. This could be done by measuring the values $C_B$, $C_P$, $C_C$ and $C_{CF}$ for the unknown blood sample and the calibrant, in the same cartridge. After calculation of $R_C$, the calibration or standard line (curve) defined from the calibration experiment to define C1 and C2, could be used to calculate % PCV.

It will be apparent from the above that alternate functions, for example including linear relations, may also be used to represent or calculate hematocrit. For example other relationships or ratios, from the conductance data, can be used. In addition, non-linear relations can be used.

The method characterized above can, in general, be described in the following terms:

1. The method generally includes steps of:
    (a) measuring conductance of an unknown whole blood sample in a hematocrit measurement system as characterized, including measurement in a first, unfiltered, conductance measurement cell to obtain a conductance measurement $C_B$; and, measurement in a second, filtered, conductance cell to obtain a conductance measurement $C_P$; and
    (b) correlating the conductance values $C_B$ and $C_P$ to determine a hematocrit value for the unknown whole blood sample.

2. In the particular preferred method characterized, the step of correlating includes correlating with conductance values for a known calibrant solution also determined in the hematocrit measurement system as follows:
    (a) measuring a calibrant conductance in the first, unfiltered, conductance measurement cell to determine a value $C_C$; and
    (b) measuring a conductance of the calibrant solution in the second, filtered, conductance measurement cell to obtain a value $C_{CF}$.
    (c) In general, the measured values $C_B$, $C_P$, $C_C$, and $C_{CF}$ would be correlated to determine a hematocrit value for the unknown whole blood sample.

3. In a preferred step of correlating $C_B$, $C_P$, $C_C$, and $C_{CF}$:
    (a) a value $R_B$ is calculated according to the formula $R_B = C_B/C_C$;
    (b) a value for $R_P$ is calculated according to the formula $R_P$ $C_P/C_{CF}$; and,
    (c) the values $R_B$ and $R_P$ are related to one another to determine hematocrit value for the unknown whole blood sample.

4. A particular process characterized herein concerns:
    (a) relating $R_P$ and $R_B$ to obtain an $R_G$ value as follows: $R_G = R_B/R_P$; and,
    (b) then correlating $R_G$ to hematocrit.

5. A particular process characterized herein for correlating $R_G$ to hematocrit, is determining hematocrit according to the formula:

$$\text{Hematocrit} = R_G(C1) + C2;$$

wherein C1 and C2 are constants empirically derived for the system involved, typically derived from experimental evaluations using the same or similar calibrant and selected hematocrit standards.

In this section, the methods and apparatus have been discussed for operation and use to determine hematocrit, based upon measurement of "conductance" or "conductivity." As indicated previously, conductance is, in general, the reciprocal of resistance. Thus, the same approach and calculations can be conducted, based upon measurement of "resistance." Herein, when it is stated that a "conductance" or "conductivity" value can be measured, the term is meant to include measurement of "resistance," and its utilization in functions to correlate the types of values discussed.

Herein above, general method steps for conducting hematocrit measurement are described. There is no intent to indicate the precise order of steps in the recitations provided. Indeed, herein no specific order of steps is meant in the general recitations of hematocrit measurement experiments, unless specifically and expressly stated. In general, whether measurements of the calibrant are taken first, or measurements of the unknown whole blood are taken first, will be a matter of choice, based upon convenience of operation of the equipment. Some equipment may be configured so that one of the two sets of measurements defined would ordinarily or even necessarily be taken first.

Also, above reference was made to various ratios for example $R_B=C_B/C_C$. Of course an inverse of these ratios could alternatively have been used, provided the system was appropriately established. This should be apparent from the discussions and techniques outlined above.

III. Alternate Configurations for the Hematocrit Measurement Arrangement

A. FIGS. 4 and 5; Configurations to Use Fewer Channels.

As indicated above, the arrangement of FIG. 2 utilizes a total of four electrodes in the arrangement 17, two in each cell; and, four electrical traces, leads or channels for operation of those electrodes, indicated generally at 22a and 22b. In some instances it may be desirable to utilize fewer traces, leads or channels for control of the conductance experiment, by remote analytical equipment. Approaches to accomplishing this are provided in the alternate embodiments of FIGS. 4 and 5.

Figure 4:
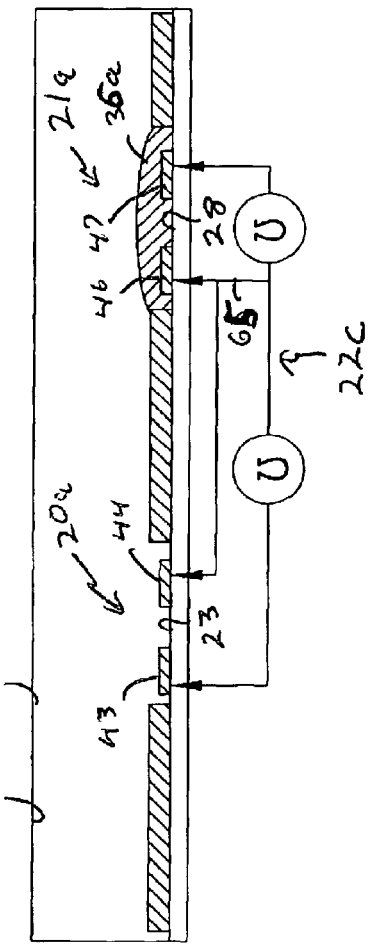
FIG. 4 is a schematic diagram of the first alternate embodiment of a conductance measurement system according to the present disclosure.

Attention is first directed to FIG. 4, which depicts an alternate hematocrit measurement system 17a, that could be used in place of arrangement 17, FIG. 1. The alternate hematocrit measurement system 17a generally comprises, within section 40 of fluid flow channel 13, a first, unfiltered, conductance measurement cell 20a and a second, filtered, conductance measurement cell 21a. Since the second conductance measurement cell 21a is a filtered cell, it includes filter 36a therein and may be generally analogous to (or even the same as) cell 21, described above. The first cell 20a may also be similar to (or even the same as) cell 20, FIG. 2.

The difference between the embodiment of FIG. 2 and the embodiment of FIG. 4, relates to the nature of control arrangement 22c (FIG. 4) versus 22a and 22b (FIG. 2). Again, for operation of the arrangement of FIG. 2, the control arrangement 22 utilizes a four electrode system that involves making measurements on four separate channels; i.e., using four separate electrical leads to control equipment.

The arrangement of FIG. 4 indicates how conductance measurements using four electrodes 43, 44, 46, 47 (in two cells) can be made with only a three channel or lead approach; that is using a four electrode/three channel (or lead) configuration. This approach may be useful, if the cartridge 10 or analytical equipment has limited channels or leads available for hematocrit evaluation.

In the arrangement 17a, of FIG. 4, the electrodes 44, 46 of the two cells 20a, 21a are shorted together on the sensor chip and therefore share a measurement channel 65. The conductivity measurements would be performed exactly as described for the arrangement of FIG. 2. The differences would be that: (1) in the design of FIG. 4, the conductance between electrode 44 and the pair of electrodes 46 and 47 (under the filter 36a) would typically be selected to be much less than the conductance between electrodes 43 and 44; and, (2) the conductance between electrode 43 and the pair of electrodes 46 and 47 (under the filter 35a) would typically be much less than the conductance between electrodes 43 and 44.

Figure 5:
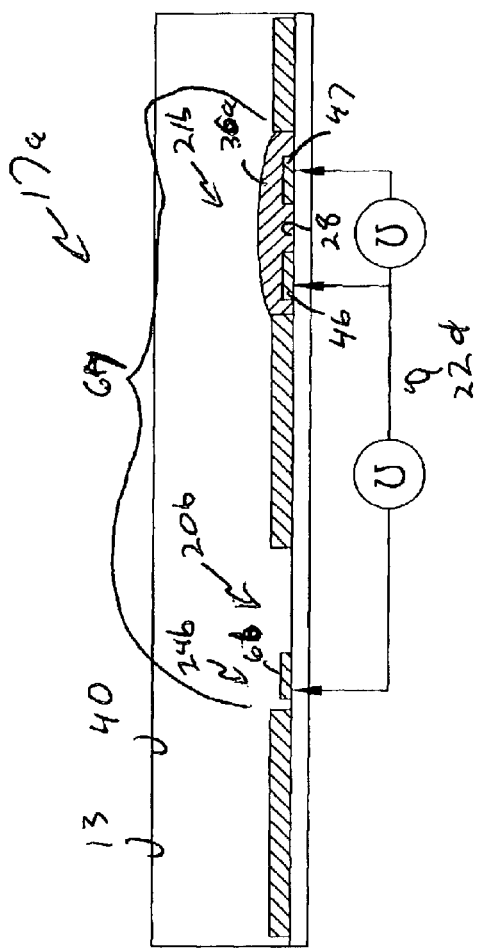
FIG. 5 is a schematic diagram of the second alternate embodiment of a conductance measurement system according to the present disclosure.

A second alternate embodiment is indicated in FIG. 5, in which an alternate hematocrit measurement system 17b is also shown. This measurement system 17b could be used in place of the arrangement 17, FIG. 1. As a result, the alternate hematocrit system 17b would generally comprise, within section 40 of fluid flow channel 13, a first conductance measurement cell 20b and a second conductance measurement cell 21b. The second conductance measurement cell 21b would be a filtered cell, having filter 36a therein, and may be generally analogous to cell 21, described above. The first conductance measurement cell 20b, on the other hand, would differ from cell 20 of FIG. 2 in that it includes an electrode arrangement 24b including only a single electrode 66 (as opposed to a pair of electrodes 43, 44 FIG. 2). Of course, in fact, the first conductance measurement cell 20b utilizes as a second electrode, the second cell 21b. This means that in the second embodiment, the actual "unfiltered" cell extends over the region 67. It also means one of the electrodes in the first, unfiltered cell 20b is in fact an electrode positioned under a filter 36a. However the cell length 67 is so long, relative to the depth of the filter 36a, then for all practical purposes in the hematocrit measurement the filtration affect of the filter 36a on a measurement of conductance for cell 20b is negligible. This means that, for practical purposes, the first cell 20b is indeed an unfiltered cell.

This alternative could be described as a three electrode/three channel (or lead) configuration. In this configuration, the conductance between electrodes 43 and 44 (FIG. 2) would be replaced by measuring the conductance between electrodes 66 and 46 (or 47). In this case, the measurement and calculations would be the same as discussed above for FIG. 2. The only difference would be that with this design, the conductance between electrode 46 and the blood or calibrant (through the filter 36a) must be much greater than the conductance between electrode 66 and an outer surface of the filter 36a.

In FIG. 5, the control circuit is indicated at 22d.

Figure 7:
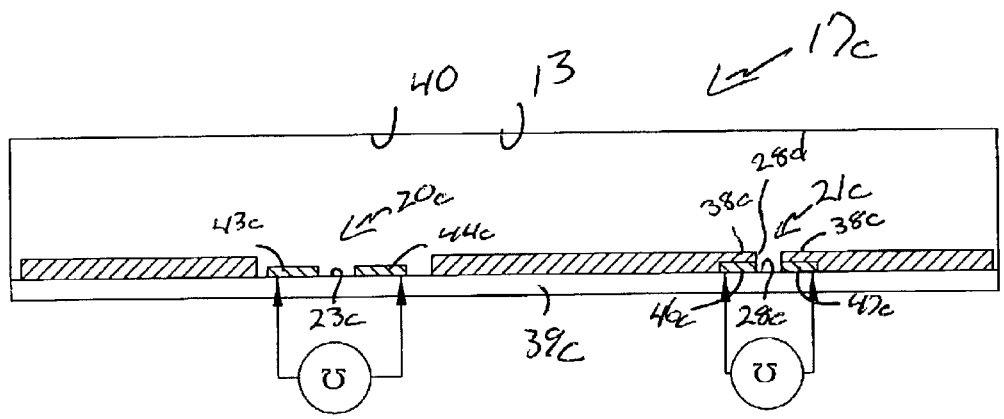
FIG. 7 is a schematic diagram of a third alternate embodiment of a conductance measurement system according to the present disclosure.
Figure 8:
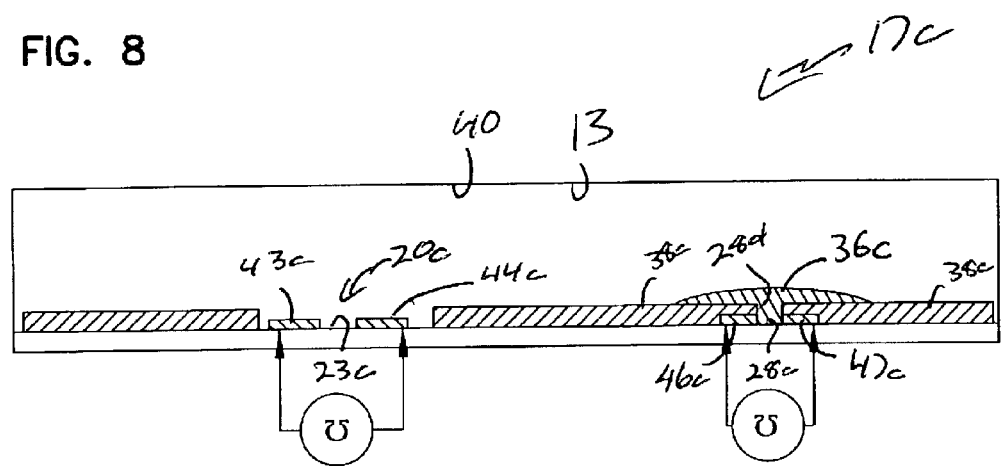
FIG. 8 is a schematic diagram of a fourth alternate embodiment of a conductance measurement system according to the present disclosure.

B. FIGS. 7 and 8; Alternate Filtered Cell Configurations.

Attention is now directed to FIG. 7. In FIG. 7 in hematocrit measurement system 17c is depicted. The system 17c generally comprises a substrate 39c having a first, unfiltered conductance measurement cell 20c and second, filtered, conductance measurement cell 21c thereon. In general, the first, unfiltered, conductance measurement cell 20c comprises electrodes 43c and 44c, with gap 23c therebetween; and, the second, filtered, conductance measurement cell 21c comprises electrodes 46c and 47c, with gap 28c therebetween.

In general, system 17c would be constructed similarly to the arrangement 17, FIG. 2 except for the following:

A conductor, which will eventually form electrodes 46c, 47c, would typically be printed on to ceramic substrate 39c, as a single continuous piece. The conductor would be covered, completely, by a dielectric 38c. A laser then would be directed to cut through both the dielectric 38c and the conductor, to create the two opposed electrodes 46c, 47c, separated by gap 28c and also gap or slit 28d in the dielectric 38c. As an example, each of the electrodes 46c, 47c could be made to be about 25 microns high and about 125–500 microns long. The materials could be sized that such the laser cut would leave a gap no greater than 50 microns, for example 10–25 micron gap, 28c between the electrodes. Thus each electrode would have an exposed surface area of about 3125 to 12500 sq. microns.

If the electrode gap 28c (and dielectric gap 28d) limited to about 10 microns, it is possible that red blood cells (which are about 6–8 microns in diameter) would have a difficult time diffusing into gap 28c, and thus no additional filter would be needed. Alternatively, in some instances it may be possible to make the gap 28c even smaller than 10 microns across. In this embodiment, the dielectric 38c is the filter material. Such a filter will sometimes be referred to herein as a cut or slit dielectric filter, or by variants thereof.

Attention is directed to FIG. 8, which depicts hematocrit measurement system 17c in accord with FIG. 7, except with a filter material 36c positioned over, and filling gap 28c and slit 28d. For example, for filter 36c a hydrogel or microporous membrane could be used.

It is noted that the arrangements for FIGS. 7 and 8 are depicted utilizing a separate channel for each electrode, similarly to the arrangement of FIG. 2. Of course the variations of FIGS. 4 and 5, discussed above, could be applied in connection with the embodiments of FIGS. 7 and 8.

IV. Additional Discussion Regarding the Cartridge 10.

A hematocrit measurement system 17 (or 17a, 17b, 17c) as generally discussed above in connection with FIGS. 1–7 can be incorporated into a cartridge 10 which is dedicated to hematocrit measurement, i.e., which does not allow for measurement of any other liquid parameter (i.e., blood characteristic). On the other hand, the hematocrit measurement system 17 (or 17a, 17b, 17c) may be positioned within a cartridge 10 that is configured for measuring other liquid or sample characteristics. Such an arrangement is depicted in FIG. 1.

Referring again to FIG. 1, cartridge 10 generally includes a base structure 72 including mounting structure or flanges 72a to facilitate mounting an analytical equipment, for use.

The cartridge 10 further includes a first analytical sensor arrangement 77, comprising sensors 77a and a counter or reference electrode 84. The number and type of sensors 77a may be varied, and is a matter of choice, depending upon the types and number of analyses to be conducted. In general terms, the sensors would be selected from electrical, electrochemical, enzymatic, optical and mechanical sensors. Descriptions relating to this are provided for example in the Thomberg, et al. application and the Kee Van Sin application referred above.

As an example, the sensors 77a can be chosen to determine: oxygen ($pO_2$) content, creatinine content, blood urea nitrogen (BUN) content, glucose content, sodium ($Na^+$) content, acidity (pH), carbon dioxide ($pCO_2$) content, calcium ($Ca^{+2}$) content, potassium ($K^+$) content, chloride ($Cl^-$) content, lactate content, coagulation evaluations or other desired information.

Cartridge 10 includes a plurality of electrical termini 86 some of which are in electrical communication with traces, not shown, that communicate with the hematocrit measurement arrangement 17 (or 17a, 17b) for control of the hematocrit testing. In general, selected ones of the electrical termini 86 and any electrically conductive traces that provide such communication, will generally be referred to herein as the hematocrit electrically conductive arrangement, leads, or channels.

Other ones of the electrical termini 86 are selected to provide communication with traces, not shown, that communicate with the analytical sensor arrangement 77, for control of the (non-hematocrit) sensors 77a. In general, selected ones of the electrical termini 86 and any electrically conductive traces that provide such communication, will be generally referred to herein as the non-hematocrit sensor electrically conductive arrangement, leads or channels.

Still referring to FIG. 1, the cartridge 10 depicted also includes, as part of the sensor arrangement 77, an analytical spur arrangement 93, comprising the plurality (eight being shown) of analytical cells 96, configured for conduct, if desired, of a titration experiment as described in the Kee Van Sin application previously incorporated herein by reference. Of course, appropriate ones of termini 86 would be in electrical communication with traces (not shown) and the analytical spur arrangement 93, for conduct of such tests. Such electrical termini 86 and associated electrically conductive traces, will be generally referred to herein as the titration cell electrically conductive arrangement, leads or channels.

Figure 6:
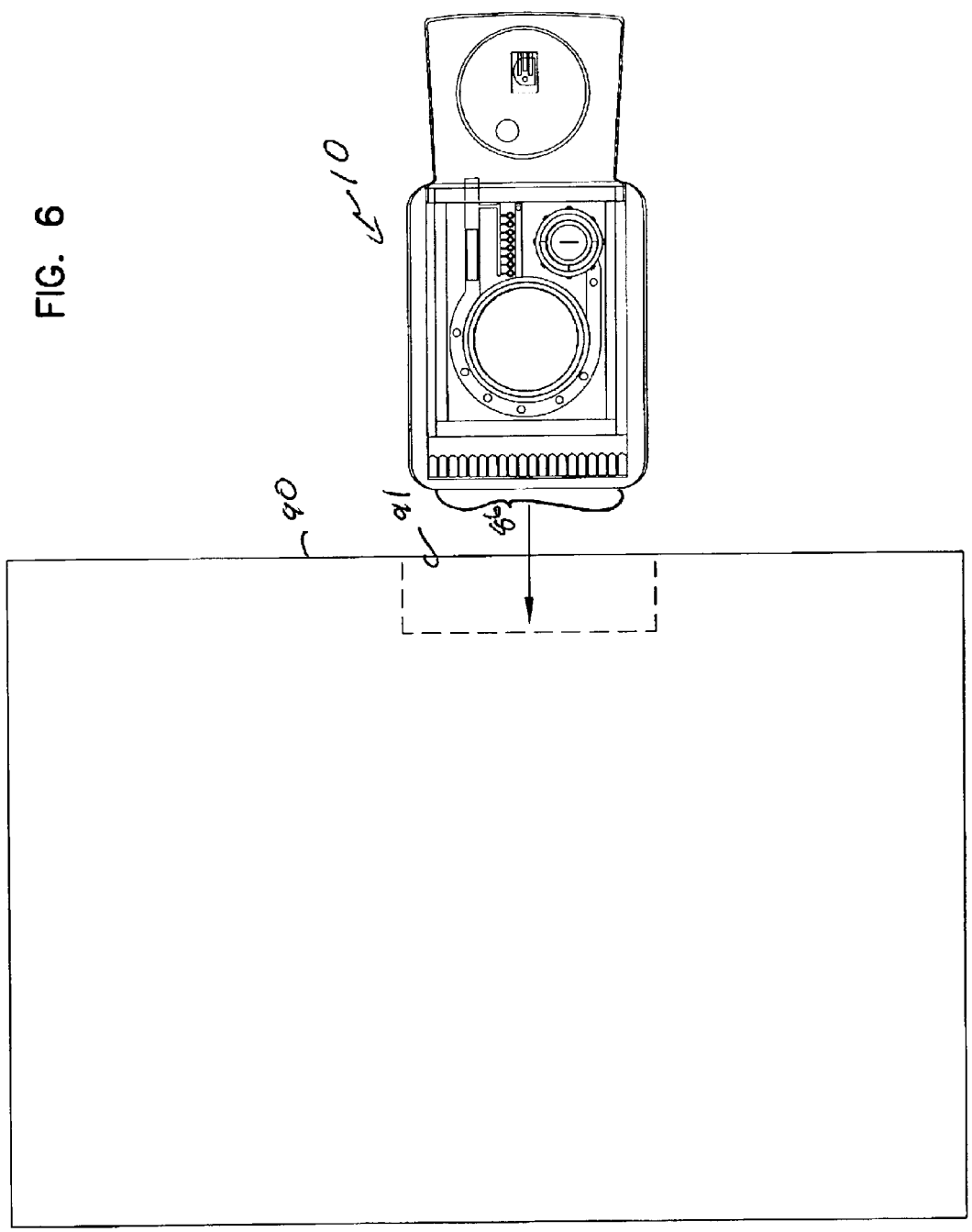
FIG. 6 is a schematic diagram of an analysis cartridge according to the present disclosure shown being inserted into an analytical base station, for use.

Of course the various termini 86, are positioned for contact with analytical equipment or modules, for operation. Such an arrangement is indicated schematically, in FIG. 6. Referring to FIG. 6, cartridge 10 is depicted being inserted into an analytical equipment base 90, in receiver 91. When such an insertion occurs, termini 86 would come into electrical connection with appropriate portions of the analytical base equipment 90, for operation.

From the above description, the potential importance of reducing the number of channels necessary for operation of the hematocrit arrangement 17, as discussed above in connection with FIGS. 4 and 5, will be more apparent. It is possible, for example, that base analytical equipment which may pre-exist this development, is already configured to operate with a limited number of leads or termini still available, i.e., less than 4, or with a limited number of programmable channels (i.e., less than 4) still available for operation of the hematocrit arrangement 17 (17a, 17b, 17c). The option provided by embodiments 4 and 5, allows for implementation of the techniques described herein, even under such circumstances.

It is noted that the particular order and spacing of the cells 20, 21 in FIG. 1, is a matter of choice. Many variations from the example shown are feasible, using the principles described herein. Alternate shapes of the channel 13, for example, are possible. Also, various ones of sensors 77a could be placed in a different order and in deed some could be positioned between the cells 20, 21.

V. Typical Materials and Methods of Assembly.

In sections I–IV, specific detail and techniques directly related to configuration and operation (conduct) of a hematocrit determination were provided. In this section other general descriptions relating to the cartridge 10 are provided. The information is intended to be general in nature, and some is analogous to that found in the Thomberg, et al. application and the Kee Van Sin application, again incorporated herein by reference.

In general, the sensors and electrodes (77, 84) may be of a variety of types. One can, for example, use conventional sensors selected from: ion selective electrode (potentiometric) sensors; amperometric sensors; conductometric sensors; and, enzymatic sensors.

If the fluid sample is blood, for the sensors 77 in the flow channel 13 (i.e., for non-hematocrit sensors not part of the hematocrit measurement arrangement 70) typically usable constructions include ion selective electrode sensors to measure pH and $pCO_2$. With current technology, a $pO_2$ sensor would typically be an amperometric sensor. For blood electrolytes, for example, sodium ($Na^+$) sensors, calcium ($Ca^{+2}$) sensors, and potassium ($K^+$) sensors, ion selective electrode sensors are typically used. Chloride ($Cl^-$) can be measured, in typical implementations, with an ion selective electrode sensor. Glucose, blood urea nitrogen (BUN) and creatinine have typically been measured using enzymatic sensors. Measurements of blood coagulation are typically conducted using conductometric sensors.

A titration experiment provided in the analytical cells 96, could for example be a heparin titration; in which each cell, for example, includes a heparin sensor and a selected amount of titration agent or heparin. As described in the Kee Van Sin application, a titration could be conducted using an ion selective sensor for heparin, and a titration agent such as protomine.

In some instances it may be desirable to store certain types of sensors in contact with solution ("wet-stored"), or separate from solution ("dry-stored"). Also, it may be desirable to inject both a blood sample and calibrant sample, at different times, through the channel 13. Techniques for creating selected fluid flow or location, and valve control over fluid flow, are described in the Thornberg, et al. application. In that application utilization of region 97, FIG. 1 herein, as a calibrant reservoir, is described.

A typical cartridge 10 comprises a multi-component structure including: a base structure or housing; and, an enclosed analytical substrate. The housing would typically comprise molded plastic components, for example polycarbonate components. The analytical substrate would typically comprise a ceramic substrate having deposited thereon: appropriate electrically conductive materials for formation of the sensors and electrical traces; any dielectric required; and, any needed chemical or enzyme materials, for operation of the various sensors and cells. The typical cartridge would comprise snap-together components, or adhesively secured components. Dimensions for a cartridge would typically be no more than 100 sq. cm., and usually no more than 80 sq. cm., for example 50 sq. cm., or less, as a cartridge perimeter or foot print area, with a total height (not including an injection syringe) or typically no greater than about 3 cm.

The molded plastic components would include appropriate molded passages or vanes to define the various internal structure such as flow channels, spurs and cells.

A typical cartridge would be configured to hold, during operation, a total unknown fluid sample having a volume of no greater than 3 milliliters (ml), typically no more than 200 microliters ($\mu l$).

As indicated above, the material for the filter material 36 may comprise a hydrogel. In general a hydrogel is a water swollen cross linked polymerically structured material, such as a polyvinyl alcohol (PVA). A hydrogel is typically made by dissolving into solvent, dispensing over the electrodes and then drying. The gel can then be re-hydrated in wet or humid environment if necessary, to achieve desired performance. While such a hydrogel is permeable to the red blood cells, diffusion of the red blood cells through the hydrogel material would be relatively slow, by comparison to diffusion of plasma and plasma electrolytes. Thus, such a hydrogel could be used, with the conductance measurements being taken at a time selected to occur before there has been substantial diffusion of red blood cell material into the region between the electrodes.

In the alternative, a microporous membrane can be used for the filter material 36, as indicated above. For example polycarbonate membranes, such as those available from Osmonics of Minnetonka, Minn. 55343 can be used. Such a polycarbonate membrane typically has a pore size on the order of about 5.0 microns. Alternate pore sizes can be used, provided an appropriate filtering effect with respect to red blood cells is achieved.

Of course even the arrangement shown in FIG. 7, is a filtered cell, with a filter material comprising of dielectric material positioned with gap 28d therein. In such an embodiment, the dielectric material would be considered the filter material 36.

It is anticipated that in some instances, a manufactured cartridge could be provided with data thereon relating to its calibrant and appropriate standards C1 and C2, to be communicated to an analytical base station when the cartridge is inserted therein for use. Programming within the analytical base station could be appropriate to use this information, during conduct of a hematocrit measurement evaluation.

In preferred operation as discussed above, the cartridge 10 is used with both an evaluation of a calibrant solution and also evaluation of an unknown whole blood sample. Various flow path arrangements and valve arrangements, to control flow of calibrant solution and blood sample, within a single cartridge, are described in the Thornberg, et al. application, and may be adapted to cartridge 10 for purposes described herein. In general, it is anticipated that the calibrant solution would be evaluated in the hematocrit measurement arrangement before the whole blood sample is introduced therein, although alternatives are possible.

The above specification, examples and data provide a complete description of the use and principles of the invention. Many alternate embodiments of the invention can be made without departing from the spirit and scope of this disclosure.

What is claimed is:

1. A sample analysis cartridge comprising:
   (a) a substrate defining a top surface and a bottom surface;
   (b) a liquid sample inlet near the top surface of the substrate; and
   (c) a conductance measurement arrangement mounted on the substrate and including:
      (i) a first, unfiltered, conductance measurement cell in fluid flow communication with the liquid sample inlet; and
      (ii) a second, filtered, conductance measurement cell in fluid flow communication with the liquid sample inlet.

2. A sample analysis cartridge according to claim 1 wherein:
   (a) the conductance measurement arrangement is a hematocrit measurement arrangement; and,
   (b) the second, filtered, conductance measurement cell is a red blood cell filtered conductance measurement cell.

3. A sample analysis cartridge according to claim 2 including:
   (a) at least one, non-hematocrit, analytical sensor in fluid flow communication with the liquid sample inlet.

4. A sample analysis cartridge according to claim 2 wherein:
   (a) the second, red blood cell filtered, conductance measurement cell comprises two spaced electrodes shielded by filter material.

5. A sample analysis cartridge according to claim 4 wherein:
(a) the filter material comprises a hydrogel.

6. A sample analysis cartridge according to claim 4 wherein:
(a) the filter material comprises a microporous membrane.

7. A sample analysis cartridge according to claim 4 wherein:
(a) the filter material comprises a slit dielectric material.

8. A sample analysis cartridge according to claim 4 wherein:
(a) the spaced electrodes within the second conductance measurement cell each comprise a gold electrode; the two spaced electrodes of the second conductance measurement cell being spaced apart from one another by a distance of no greater than 0.127 mm.

9. A sample analysis cartridge according to claim 5 wherein:
(a) the filter material comprises a PVA hydrogel.

10. A sample analysis cartridge according to claim 5 wherein:
(a) the cartridge defines a perimeter area of no greater than 80 sq. cm.

11. A sample analysis cartridge according to claim 6 wherein:
(a) the filter material comprises a microporous polycarbonate membrane.

12. A sample analysis cartridge according to claim 10 wherein:
(a) the first, unfiltered, conductance measurement cell comprises two spaced electrodes.

13. A sample analysis cartridge according to claim 10, wherein:
(a) the hematocrit measurement arrangement is configured for an operational sample volume of no greater than 200 μl.

14. A sample analysis cartridge according to claim 12, wherein:
(a) the two spaced electrodes within the first, unfiltered, conductance measurement cell each comprise a gold electrode.

15. A sample analysis cartridge, comprising:
a liquid sample inlet;
a conductance measurement arrangement including:
(i) a first, unfiltered, conductance measurement cell that is a hematocrit measurement arrangement in fluid flow communication with the liquid sample inlet; and
(ii) a second, filtered, conductance measurement cell that is a red blood cell filtered conductance measurement cell in fluid flow communication with the liquid sample inlet and comprising two spaced electrodes shielded by filter material comprising a hydrogel;
wherein the cartridge defines a perimeter area of no greater than 80 sq. cm; and
wherein the first unfiltered, conductance measurement cell includes a single electrode, which is operated to measure an unfiltered conductance value by use of an electrode in the second, filtered, conductance measurement cell.

16. A method of evaluating hematocrit, comprising:
(a) measuring conductance of an unknown whole blood sample in a hematocrit measurement system including:
(i) a substrate defining a first surface and a second surface opposed to the first surface;
(ii) a first, unfiltered, conductance measurement cell on the first surface to provide a measurement value $C_B$; and
(iii) a second, red blood filtered, conductance measurement cell on the first surface to obtain a measurement value $C_P$; and
(b) correlating the conductance measurements $C_B$ and $C_p$ to determine a hematocrit value for the whole blood sample.

17. A method according to claim 16 including steps of:
(a) measuring conductance of a known calibrant in:
(i) the first, unfiltered, conductance measurement cell to obtain a conductance measurement value $C_C$; and,
(ii) the second, red blood filtered, conductance measurement cell to obtain a conductance measurement value $C_{CF}$;
(b) wherein said step of correlating comprises correlating the conductance measurements $C_B$, $C_p$, $C_C$ and $C_{CF}$ together to determine a hematocrit value for the unknown whole blood sample.

18. A method according to claim 17 wherein:
(a) said step of correlating comprises:
(i) calculating a value of $R_B$ from the formula: $R_B = C_B/C_C$;
(ii) calculating a value of $R_p$ from the formula: $R_p = C_p/C_{CF}$; and
(iii) relating $R_B$ to $R_p$ to determine a hematocrit value for the unknown whole blood sample.

19. A method according to claim 18 wherein:
(a) said step of relating $R_B$ to $R_p$ comprises:
(i) calculating $R_G$ according to the formula $R_G = R_B/R_P$; and
(ii) determining hematocrit by comparing $R_G$ to an $R_G$ function previously established using standards.

20. A method according to claim 19 wherein:
(a) said step of determining hematocrit by comparing $R_G$ comprises determining hematocrit according to the formula:

$$\text{Hematocrit} = R_G(C1) = C2$$

wherein C1 and C2 are constants empirically derived for the hematocrit measurement system.

* * * * *